United States Patent
Acker et al.

(10) Patent No.: US 7,812,281 B2
(45) Date of Patent: Oct. 12, 2010

(54) METHOD FOR GENERATING OPTICALLY PERCEPTIBLE LASER-INDUCED CRACKS IN BRITTLE MATERIAL

(75) Inventors: Stefan Acker, Waldeck (DE); Juergen Weisser, Jena (DE); Ronny Ullmann, Altenberga (DE)

(73) Assignee: JENOPTIK Automatisierungstechnik GmbH, Jena (DE)

( * ) Notice: Subject to any disclaimer, the term of this patent is extended or adjusted under 35 U.S.C. 154(b) by 451 days.

(21) Appl. No.: 11/777,440

(22) Filed: Jul. 13, 2007

(65) Prior Publication Data

US 2008/0011724 A1 Jan. 17, 2008

(30) Foreign Application Priority Data

Jul. 14, 2006 (DE) .................. 10 2006 033 217

(51) Int. Cl.
*B23K 26/40* (2006.01)
*C03C 23/00* (2006.01)
*G01N 21/896* (2006.01)

(52) U.S. Cl. .................. 219/121.69; 65/112

(58) Field of Classification Search .......... 65/112; 83/16; 427/555; 219/121.69; 216/65; 264/400, 264/482
See application file for complete search history.

(56) References Cited

U.S. PATENT DOCUMENTS

| 3,453,097 | A | * | 7/1969 | Hafner | ......... 65/112 |
|---|---|---|---|---|---|
| 3,777,143 | A | | 12/1973 | Winans et al. | |
| 5,427,724 | A | * | 6/1995 | Zimmerman | ......... 264/134 |
| 5,609,284 | A | * | 3/1997 | Kondratenko | ......... 219/121.73 |
| 5,776,220 | A | * | 7/1998 | Allaire et al. | ......... 65/112 |
| 7,223,936 | B2 | * | 5/2007 | Acker et al. | ......... 219/121.67 |
| 2002/0195560 | A1 | | 12/2002 | Yonushonis | |
| 2003/0019243 | A1 | * | 1/2003 | Biethmann et al. | ......... 65/112 |

FOREIGN PATENT DOCUMENTS

| JP | 63-153457 A | * | 6/1988 |
| JP | 08-219963 A | * | 8/1996 |
| JP | 2000-211298 A | * | 8/2000 |

OTHER PUBLICATIONS

Machine translation of Japan Patent No. 8-219,963, Mar. 2010.*
Machine translation of Japan Patent No. 2000-211,298, Mar. 2010.*

* cited by examiner

*Primary Examiner*—Geoffrey S Evans
(74) *Attorney, Agent, or Firm*—Frommer Lawrence & Haug LLP

(57) ABSTRACT

The invention is directed to a method for generating optically perceptible laser-induced cracks in brittle material, wherein a laser beam, followed by a coolant jet, is guided relative to the surface of the brittle material in order to advance a crack trail into the material starting from an initial crack, and wherein a marking agent which penetrates into the crack during the formation of the crack so as to make the latter visible is mixed with the coolant.

1 Claim, 1 Drawing Sheet

METHOD FOR GENERATING OPTICALLY PERCEPTIBLE LASER-INDUCED CRACKS IN BRITTLE MATERIAL

CROSS-REFERENCE TO RELATED APPLICATION

This application claims priority of German Application No. 10 2006 033 217.2, filed Jul. 14, 2006, the complete disclosure of which is hereby incorporated by reference.

BACKGROUND OF THE INVENTION a) Field of the Invention

The invention is directed to a method for generating optically perceptible laser-induced cracks in brittle material as is known generically from DE 101 29 876 C1.

b) Description of the Related Art

Methods for thermal laser beam separation (TLS methods) have been widely practiced for severing brittle material, and there are many publications and patents based on the fundamental method described in DE-AS 12 44 346 which further develop and modify this fundamental method especially to improve the quality of the severing edge and to make the process more efficient.

The various generic methods have in common with the method according to DE-AS 12 44 346 that the material is heated along the desired severing line to a temperature below the melting temperature by passing a laser beam over it, and high thermal stresses are generated along the severing line by a coolant jet following the laser beam such that a crack is driven along the severing line (crack trail) in the material proceeding from an initial crack.

Depending on the particulars of the individual method and the parameters of the method and material, the crack can penetrate completely through the material, particularly when its thickness is small, or may only form a depth crack. Final severing along the severing line is then generally carried out by application of mechanical force along the crack trail immediately thereafter or subsequently so that the material breaks.

Since, in contrast to mechanical cutting processes or laser sublimation methods, there is no removal of material and therefore also no change in the surface structure, the visibility of the severing line is very limited in spite of the crack formation.

In order to ensure a uniform application of force on both sides of the crack trail, a device provided for breaking is oriented to the crack trail. Insofar as the breaking process immediately follows the generation of the crack, the breaking device can be directed so as to be oriented to the guiding of the laser and of the coolant nozzle. Provided that there is no misalignment and the crack is actually still advanced continuously, the breaking edge can be expected to be free from break defects.

However, when the breaking is not to be carried out until later at a location other than that where the crack was generated, it is important that the crack is visible or optically detectable in order that a breaking device or other processing devices for process steps preceding the separation, such as a partial coating or outfitting, can be oriented to the crack trail.

DE 101 29 876 C1 discloses a process by which a permanently visible mark trail is realized along a crack trail (referred to in this case as a scribing trail) in glasses in that a coating is at least partially applied to the crack trail after the laser-induced scribing and prior to the breaking process. Visibility is ensured by dyeing the coating to a color that differs from that of the surfaces of the glass elements and/or by an elevation of the surface on the crack trail attributable to the layer thickness.

It is possible to remove the coating, for example, after the breaking process by washing the individual glass elements. The possibilities suggested for applying the coating to the crack trail (application of a marking trail) are either to thoroughly coat the entire crack trail or to apply the coating at determined distances along the length of the crack trail so that, e.g., only marking points need be placed.

According to DE 101 29 876 C1, the coating can be applied by a jet device, a pen, or a spraying device. When a jet device is used, a liquid which hardens is applied to the crack trail. Application of a coating by means of a jet requires at least one jet device with an application nozzle. According to a described embodiment example, this jet device as well as the device for laser-induced scoring are stationary so that the necessary relative movement is carried out by the glass element.

The described method is disadvantageous in that the marking trail can deviate from the crack trail due to misalignment and the marking trail is applied regardless of whether or not a crack trail has been generated at all. The processing steps following the generation of the crack are not oriented to the actual progression of the crack trail, but rather to a marking trail with a reference path identical to the intended path of the crack trail whose presence is assumed. Discrepancies between the actual paths of the marking trail and of the crack trail lead to fluctuations in the quality of the processing steps following the generation of the crack.

For inspecting cracks, particularly in non-magnetizable workpieces such as ceramics, it is known to use dye penetration methods, as they are called. In this case, workpieces are prepared for crack inspection in a manner known per se in that they are sprayed with dyes, particularly fluorescent dyes, which penetrate into the cracks through capillary forces and therefore are not removed when the surfaces are subsequently cleansed of dye. Accordingly, the cracks are detectable by means of the deposited dyes either immediately or after subsequent treatment with a developer and a predetermined developing time under UV light or visible light by direct visual contact or by automatic image processing. The use of the dye penetration method is known for detecting defects within the framework of quality control.

OBJECT AND SUMMARY OF THE INVENTION

It is the primary object of the invention to show a method for making laser-induced crack trails visible in which the actual path of the crack trail is marked so that orientation can be carried out based on the subsequent processing steps of the method.

Another object of the invention is to suggest a method by which the generation of crack trails can be detected for process control.

This object is met in a method for generating optically perceptible laser-induced cracks in brittle materials according to the invention comprising the steps of guiding a laser beam, followed by a cooling jet relative to the surface of brittle material in order to advance a crack trail into the material starting from an initial crack, making the crack trail visible by applying a marking agent to the surface of the material in the area of the crack trail and allowing the marking agent to penetrate into the crack and subsequently removing the marking agent from the surface so that only the marking agent that has penetrated into the crack remains.

It is essential to the invention that a marking agent is deposited directly in the crack after or during the formation of the crack along the crack trail so that the true actual path of the crack trail is visible and the crack depth is also optically perceptible in case of transparent material.

The invention will be described in more detail in the following with reference to an embodiment example shown in the drawing.

DESCRIPTION OF THE PREFERRED EMBODIMENTS

Figure 1:
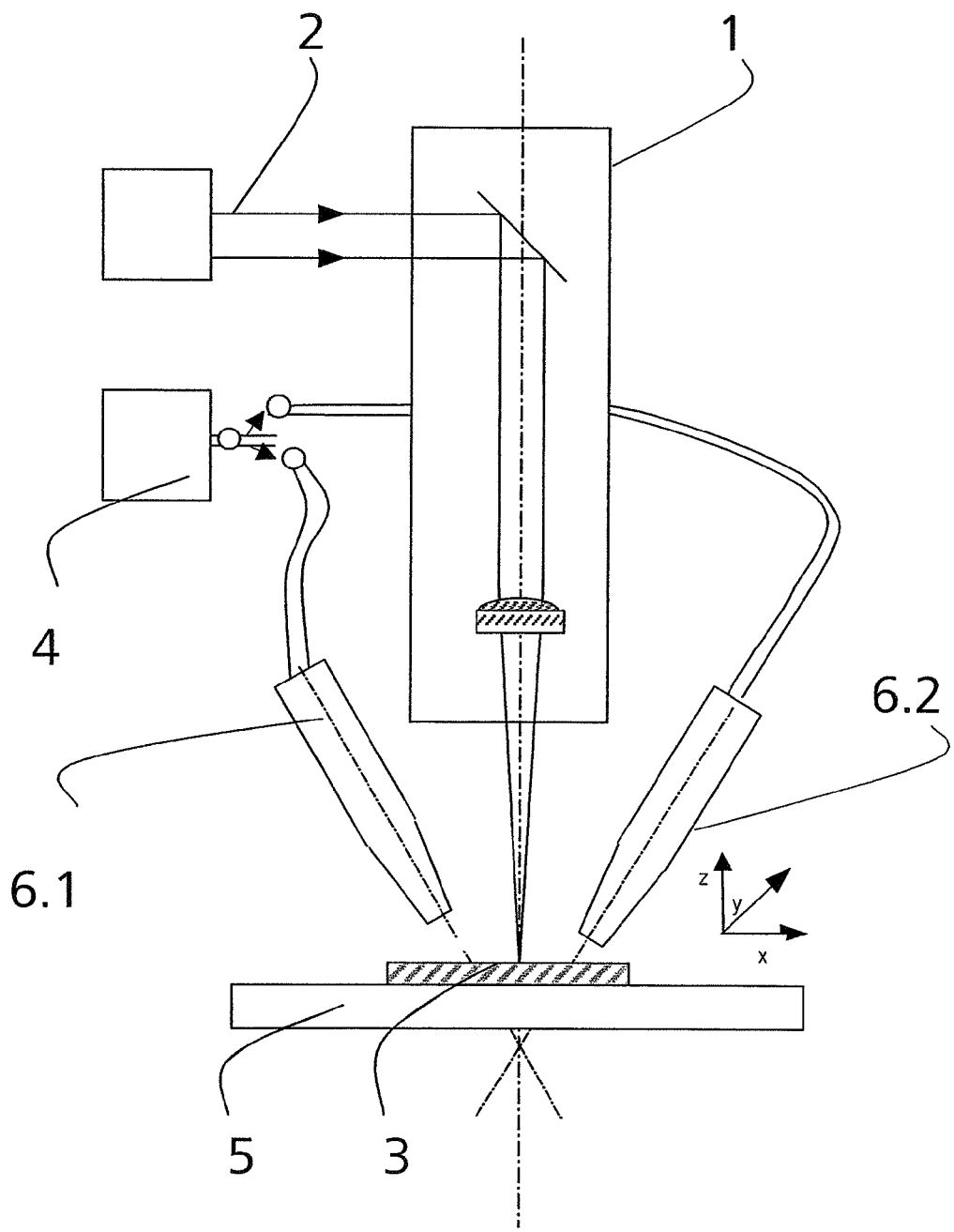
FIG. 1 shows the basic construction of an advantageous device for carrying out the method.

The device shown in FIG. 1 comprises a laser machining head 1 by which a laser beam 2 is directed to the surface of a workpiece 3 of brittle material, e.g., ceramic or glass. In order to generate the necessary relative movement between the laser beam 2 and the workpiece 3, the latter is positioned on a movement system 5.

Further, at least one cooling nozzle 6.1, 6.2 is connected to a supply reservoir 4 and directs a coolant jet to the surface of the workpiece 3 identical to the laser beam 2. Two coolant nozzles 6.1, 6.2 are advantageous so that they may be activated alternately when the direction of the relative movement is changed.

The TLS method is carried out in a manner known per se, i.e., starting from an initial crack, the laser beam 2, followed by the coolant jet, is guided along the desired severing line so that a crack trail is generated along this severing line, this crack trail extending to a depth in the workpiece 3 depending on the material parameters, particularly the thickness of the workpiece, and the process parameters of the method.

To make the corresponding crack trail visible, a dye-containing chemical substance (marking agent) is added to the coolant and is drawn into the crack as the crack propagates. The dyes depositing in the crack are not removed during subsequent cleaning of the workpiece surface so that the path of the crack (crack trail) and—insofar as the material is transparent in the visible region—its depth can be detected. Obviously, the dyes must differ from the color of the material in the spectral range of view.

Accordingly, suspension of the crack trail or fluctuation in the crack depth can be determined so that a perfect process control is possible. Based on the optically detectable crack, the subsequent processing steps can be oriented to its actual path (crack trail).

The admixture of the marking agent in the coolant is particularly advantageous because the marking agent is literally sucked in as the crack is formed. Further, no additional process step for marking is necessary and also no additional expenditure on apparatus is required.

Purified water with certain additions for process optimization is normally used as coolant for TLS methods.

Commercially available crack checking agents for nondestructive crack testing can be used as marking agent. The intensity of the dyeing and therefore the visibility of the crack and its permanence can be adjusted by way of the mixture ratio of coolant and marking agent.

As an alternative to the addition of marking agent to the coolant, the marking agent can also be applied in a separate process step, e.g., by immersion, spraying or painting. However, the duration of the process as a whole is lengthened by the additional process step.

The person skilled in the field of the present invention will appreciate that the invention is not limited to the details of the embodiment forms mentioned above by way of example and that the present invention can be embodied in other specific forms without departing from the scope of the invention as set forth in the appended claims.

What is claimed is:

1. A method for generating optically perceptible laser-induced cracks in brittle material, comprising the steps of:
    guiding a laser beam, followed by a coolant jet, relative to the surface of brittle material in order to advance a crack trail into the material starting from an initial crack;
    making the crack trail visible by applying a marking agent to the surface of the material in the area of the crack trail; and
    allowing the marking agent to penetrate into the crack and subsequently removing the marking agent from the surface so that only the marking agent that has penetrated into the crack remains,
    wherein the application of the marking agent is carried out by spraying on the material, and
    wherein the spraying is carried out during the generation of the crack in that the marking agent is mixed with the coolant.

* * * * *